US00PP13305P3

(12) United States Plant Patent
Vandenberg

(10) Patent No.: US PP13,305 P3
(45) Date of Patent: Dec. 3, 2002

(54) ROSE PLANT NAMED 'YOPIDAR'

(75) Inventor: Cornelis P. Vandenberg, Salinas, CA (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 09/821,996

(22) Filed: Mar. 31, 2001

(65) Prior Publication Data

US 2002/0144315 P1 Oct. 3, 2002

(51) Int. Cl.[7] ..... A01H 5/00

(52) U.S. Cl. ..... Plt./137

(58) Field of Search ..... Plt./137, 130, 136

*Primary Examiner*—Bruce R. Campell
*Assistant Examiner*—June Hwu
(74) *Attorney, Agent, or Firm*—C. A. Whealy

(57) ABSTRACT

A distinctive cultivar of Hybrid Tea Rose plant named 'Yopidar', characterized by its glossy dark green leaves; long and dark red stems; large dark pink-colored flowers; and good postproduction longevity.

1 Drawing Sheet

BOTANICAL CLASSIFICATION/CULTIVAR DESIGNATION

*Rosa hybrida* cultivar Yopidar.

BACKGROUND OF THE INVENTION

The present invention relates to a new and distinct cultivar of Hybrid Tea Rose plant, botanically known as *Rosa hybrida*, commercially produced as a cut flower, and hereinafter referred to by the name 'Yopidar'.

The new cultivar is a product of a planned breeding program conducted by the Inventor in Salinas, Calif. The objective of the breeding program was to develop new cut Rose cultivars with attractive flower petal colors, long and strong stems, dark green leaves and good postproduction longevity.

The new cultivar originated from a cross made by the Inventor in 1996 of the Rose cultivar Sonia, disclosed in U.S. Plant Pat. No. 3,095, as the female, or seed, parent with the Rose cultivar Classy, not patented, as the male, or pollen, parent. The cultivar Yopidar was discovered and selected by the Inventor as a flowering plant within the progeny of the stated cross in a controlled environment in February, 1999, in Madrid, Cundinamarca, Colombia.

Since March, 2000, asexual reproduction of the new cultivar by grafting on *Rosa Manetti* rootstocks in Madrid, Cundinamarca, Colombia, has shown that the unique features of the new cultivar are stable and reproduced true to type in successive generations of asexual reproduction.

SUMMARY OF THE INVENTION

The following traits have been repeatedly observed and are determined to be the unique characteristics of 'Yopidar'. These characteristics in combination distinguish the new Hybrid Tea Rose as a new and distinct cultivar:

1. Glossy dark green leaves.
2. Long and dark red stems.
3. Large dark pink-colored flowers.
4. Good postproduction longevity.

Plants of the Hybrid Tea Rose can be compared to plants of the female parent, the cultivar Sonia. In side-by-side comparisons conducted by the Inventor in Salinas, Calif., plants of the new cultivar differed from plants of the cultivar Sonia in the following characteristics:

1. Plants of the new Hybrid Tea Rose have larger flowers than plants of the cultivar Sonia.
2. Plants of the new Hybrid Tea Rose have dark pink-colored flower petals whereas plants of the cultivar Sonia have salmon pink-colored flower petals.

Plants of the Hybrid Tea Rose can be compared to plants of the male parent, the cultivar Classy. In side-by-side comparisons conducted by the Inventor in Salinas, Calif., plants of the new cultivar differed from plants of the cultivar Classy in the following characteristics:

1. Plants of the new Hybrid Tea Rose have larger flowers than plants of the cultivar Classy.
2. Plants of the new Hybrid Tea Rose have dark pink-colored flower petals whereas plants of the cultivar Classy have red-colored flower petals.

Plants of the new Hybrid Tea Rose have not been observed under all possible environmental conditions. The phenotype may vary significantly with variations in environment such as temperature, light, water status and/or fertilizer type and rate, without, however, any variance in genotype.

BRIEF DESCRIPTION OF PHOTOGRAPH

The accompanying colored photograph illustrates the new Hybrid Tea Rose plant, showing the colors as true as it is reasonably possible to obtain in colored reproductions of this type. Colors in the photograph may differ slightly from the color values cited in the detailed botanical description which accurately describe the colors of the new Hybrid Tea Rose.

The photograph comprises a side perspective view of a typical flowering stem of the new Hybrid Tea Rose grown in Madrid, Cundinamarca, Colombia.

DETAILED BOTANICAL DESCRIPTION

The following observations and measurements describe cut flowering stems of plants grown in Madrid, Cundinamarca, Colombia, in polyethylene-covered greenhouses with day temperatures ranging from 14 to 20° C., night temperatures ranging from 4 to 8° C., and light levels ranging from 3,000 to 5,000 foot-candles. Flowering stems used in the photograph and the description were about 76 days old. In the following description, color references are made to The Royal Horticultural Society Colour Chart except where general terms of ordinary dictionary significance are used.

Classification:

*Botanical.*—*Rosa hybrida* cultivar Yopidar.

*Commercial.*—Hybrid Tea Rose used as a cut flower.

Parentage:

*Female, or seed, parent.*—*Rosa hybrida* cultivar Sonia, disclosed in U.S. Plant Pat. No. 3,095.

*Male, or pollen, parent.*—*Rosa hybrida* cultivar Classy, not patented.

Propagation:

*Type.*—Cuttings grafted onto *Rosa Manetti* rootstocks.

Plant description:

*Form.*—Upright; narrow.

*Growth habit.*—Moderately vigorous.

*Plant height.*—About 101 to 117 cm.

*Plant width.*—About 25 cm.

*Stem and lateral branches* (*peduncles*).—Lateral branch length: About 101 to 117 cm. Lateral branch diameter: Base: About 8 mm. Apex: About 5 mm. Internode length: About 4.6 cm. Texture: Smooth. Strength: Strong. Color: Close to 187A. Thorns: Quantity: About 5 per 12 cm of stem. Height: About 7 mm. Width at base: About 9 mm. Shape: Deltoid. Color, immature and mature: Close to 59A.

*Foliage description.*—Arrangement: Alternate, compound with typically three to seven leaflets per leaf. Leaf length, five-leaflet leaves: Terminal leaves: About 7.4 cm. Lateral leaves: About 7.2 cm. Leaf width, five-leaflet leaves: Terminal leaves: About 4.5 cm. Lateral leaves: About 4.3 cm. Leaflet shape: Ovate. Leaflet apex: Acuminate. Leaflet base: Obtuse. Leaflet margin: Sharply serrate. Leaflet texture: Smooth, leathery, glabrous. Occasional small thorns on lower petiole and midrib of terminal leaflet, about 2 by 2 mm in size and close to 146C in color. Petiole length, 5-leaflet leaves: About 11.4 cm. Petiole diameter: At stem attachment: About 6 mm. At base of terminal leaves: About 1.5 mm. Stipules: Quantity: Two at base of petiole. Length: About 1.7 cm. Length of appendages: About 7.5 mm. Width: About 2 mm. Color: Young and mature foliage, upper surface: Darker than 147A, glossy; venation, close to 147B. Young and mature foliage, lower surface: Close to 147B; venation, close to 147C. Petiole: Upper surface: Close to 59A. Lower surface: Close to 146A; nodes, close to 59A. Stipules, upper surface: Darker than 147A. Stipules, lower surface: Close to 147B.

Flower description:

*Flower type and habit.*—Large dark pink flowers. Consistently symmetrical rosette flowers. Freely and recurrent flowering. Flowers arranged singly at terminal apices. Flowers persistent.

*Flowering season/time to flower.*—Year-round under greenhouse conditions. Depending on environmental conditions and season, time to flower is about 76 days.

*Flower diameter, fully opened.*—About 15.5 cm.

*Flower depth* (*height*), *fully opened.*—About 5.7 cm.

*Flower longevity as a cut flower.*—At least 8 days.

*Fragrance.*—Strong, typically Hybrid Tea Rose fragrance.

*Flower buds.*—Shape: Ovoid. Length: About 5.7 cm. Color: 144A to 146A.

*Petals and petaloids.*—Petaloids vary in size, but similar to petals in shape and coloration. Quantity: About 28. Length, outer petals: About 8.4 cm. Width, outer petals: About 7 cm. Shape: Roughly obovate. Apex: Slightly emarginate. Base: Obtuse. Margin: Entire or minutely crenate. Texture: Smooth, velvety. Color: When opening, upper and lower surfaces: Closest to 57A; spot, close to 5C to 5D. Fully opened, upper and lower surfaces: Closest to 57A to 57B; occasional pale yellow, 5C to 5D, central stripe towards base; petal color fading to close to 58B to 58C with subsequent development.

*Sepals.*—Quantity: Five. Length: About 5.7 cm. Diameter: About 1.1 cm. Shape: Sharply lanceolate. Apex: Elongated, acuminate. Base: Fused at receptacle. Margin: Ciliate with occasional sharply acuminate appendages. Texture: Upper surface, pubescent; lower surface, slightly pubescent. Color: Upper surface: Closest to 144B. Lower surface: 144A to 146A.

*Reproductive organs.*—Stamens: Quantity: About 115 per flower. Anther length: About 2 mm. Anther diameter: About 1 mm. Anther shape: Cordate, concave. Anther color: Close to 14A. Filament length: About 2 mm. Filament color: Close to 38A. Pollen amount: Scarce. Pollen color: Close to 17A. Pistils: Quantity: About 65 per flower. Pistil length: About 9 mm. Style color: Close to 45A. Stigma shape: Bi-lobed. Stigma color: Close to 5D. Ovary color: 145D to 155D. Receptacle height: About 1.5 cm. Receptacle diameter: About 1.7 cm. Receptacle surface: Smooth. Receptacle color: 144A.

*Seed.*—None observed.

Disease resistance: Plants of the new Hybrid Tea Rose have been observed to be somewhat resistant to Powdery Mildew.

It is claimed:

1. A new and distinct Hybrid Tea Rose plant named 'Yopidar', as illustrated and described.

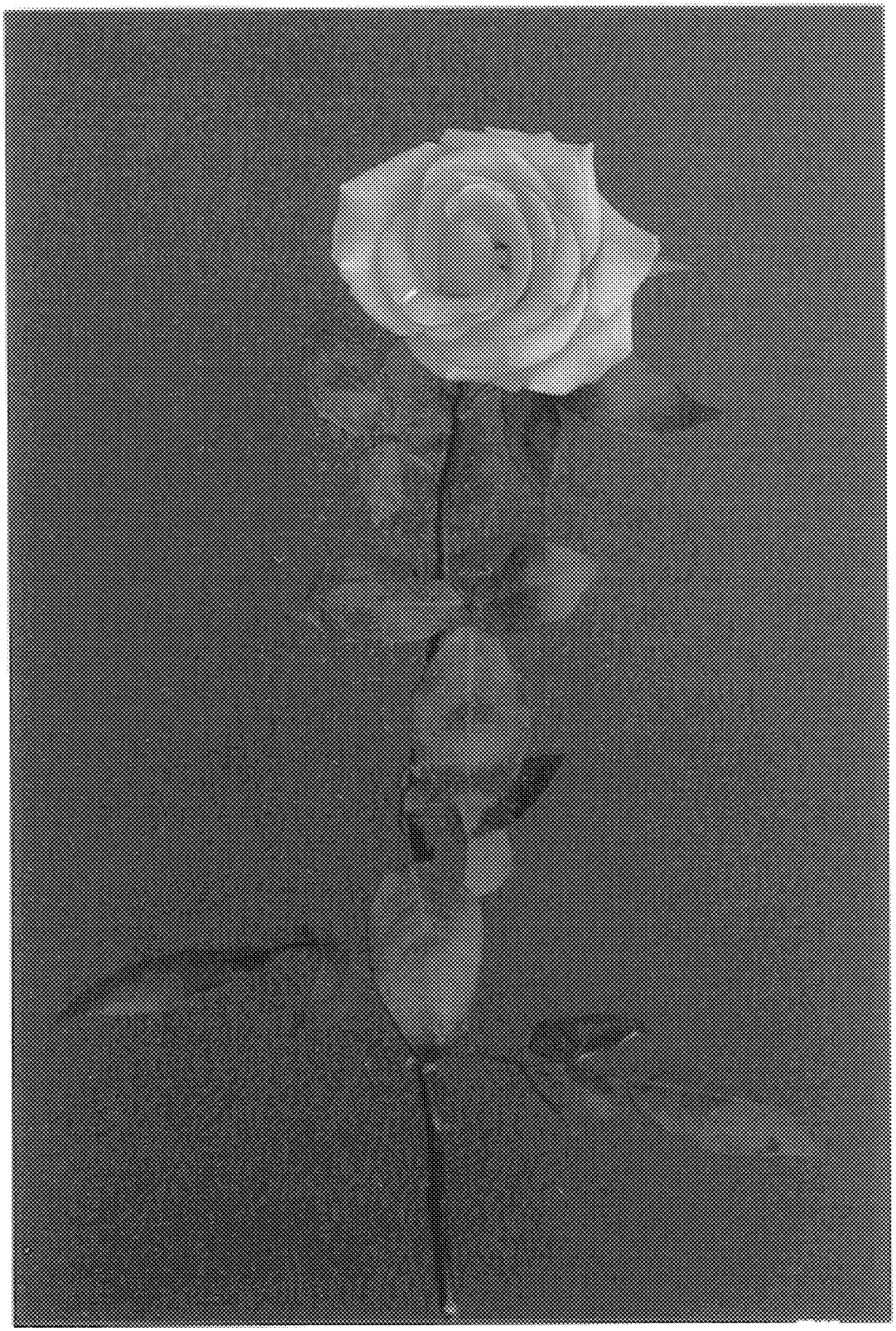

* * * * *